(12) United States Patent
Ando et al.

(10) Patent No.: US 9,646,265 B2
(45) Date of Patent: May 9, 2017

(54) MODEL UPDATING METHOD, MODEL UPDATING DEVICE, AND RECORDING MEDIUM

(71) Applicant: FUJITSU LIMITED, Kawasaki-shi, Kanagawa (JP)

(72) Inventors: Takahisa Ando, Kawasaki (JP); Takeshi Osoekawa, Ohta (JP); Seishi Okamoto, Hachioji (JP)

(73) Assignee: FUJITSU LIMITED, Kawasaki (JP)

( * ) Notice: Subject to any disclaimer, the term of this patent is extended or adjusted under 35 U.S.C. 154(b) by 12 days.

(21) Appl. No.: 14/849,771

(22) Filed: Sep. 10, 2015

(65) Prior Publication Data
US 2015/0379432 A1    Dec. 31, 2015

Related U.S. Application Data

(63) Continuation of application No. PCT/JP2013/059585, filed on Mar. 29, 2013.

(51) Int. Cl.
*G06F 19/00* (2011.01)
*G06N 99/00* (2010.01)
(Continued)

(52) U.S. Cl.
CPC ....... *G06N 99/005* (2013.01); *G06F 19/3431* (2013.01); *G06F 19/3437* (2013.01);
(Continued)

(58) Field of Classification Search
None
See application file for complete search history.

(56) References Cited

U.S. PATENT DOCUMENTS

2005/0108753 A1* 5/2005 Saidi .................. G06F 17/18
                                                           725/46
2005/0209786 A1  9/2005 Chen et al.
(Continued)

FOREIGN PATENT DOCUMENTS

JP    2001-236337    8/2001
JP    2002-109150    4/2002
(Continued)

OTHER PUBLICATIONS

Su, Chao-Ton, and Chien-Hsin Yang. "Feature selection for the SVM: An application to hypertension diagnosis." Expert Systems with Applications 34.1 (2008): 754-763.*
(Continued)

*Primary Examiner* — Vincent Gonzales
*Assistant Examiner* — David H Kim
(74) *Attorney, Agent, or Firm* — Fujitsu Patent Center

(57) ABSTRACT

A model updating method is provided. The model updating method that is executed by a computer includes calculating a score that indicates a degree of normality or abnormality of each of a plurality of pieces of data by using as a judgment model each of the pieces of data, predicting as a predicted condition whether each of the pieces of data is normal or abnormal according to score, judging whether or not the predicted condition is correct for each of the plurality of pieces of data, calculating the accuracy rate for the predicted conditions of a top specified number of pieces of data in order of decreasing abnormality as indicated by the score when the plurality of pieces of data are arranged in a specified order of score, and judging whether or not it is necessary to update the judgment model according to the accuracy rate.

9 Claims, 20 Drawing Sheets

(51) Int. Cl.
   *G06Q 50/22* (2012.01)
   *G06Q 10/04* (2012.01)
   *G06N 5/04* (2006.01)

(52) U.S. Cl.
   CPC ............... *G06N 5/04* (2013.01); *G06Q 10/04* (2013.01); *G06Q 50/22* (2013.01)

(56) References Cited

U.S. PATENT DOCUMENTS

| | | | |
|---|---|---|---|
| 2007/0112716 A1* | 5/2007 | Sapir | G06N 5/025 706/47 |
| 2010/0082506 A1* | 4/2010 | Avinash | A61B 5/7267 706/12 |
| 2010/0088264 A1* | 4/2010 | Teverovskiy | G06F 19/345 706/46 |
| 2010/0094784 A1* | 4/2010 | Varma | G06K 9/6269 706/12 |
| 2011/0078099 A1* | 3/2011 | Weston | G06F 19/24 706/12 |
| 2011/0119212 A1* | 5/2011 | De Bruin | A61B 5/00 706/12 |
| 2014/0101080 A1* | 4/2014 | Lee | G06F 19/345 706/12 |
| 2014/0279754 A1* | 9/2014 | Barsoum | G06N 7/005 706/12 |
| 2014/0344208 A1* | 11/2014 | Ghasemzadeh | G06F 19/3437 706/52 |

FOREIGN PATENT DOCUMENTS

| | | |
|---|---|---|
| JP | 2004-086896 | 3/2004 |
| JP | 2004-280450 | 10/2004 |
| JP | 2007-518972 | 7/2007 |
| JP | 2008-186113 | 8/2008 |
| JP | 2012-208710 | 10/2012 |
| WO | 2005-060608 | 7/2005 |

OTHER PUBLICATIONS

Barakat, Nahla, Andrew P. Bradley, and Mohamed Nabil H. Barakat. "Intelligible support vector machines for diagnosis of diabetes mellitus." IEEE Transactions on Information Technology in Biomedicine 14.4 (2010): 1114-1120.*

International Search Report, mailed in connection with PCT/JP2013/059585 and mailed Jun. 25, 2013 (2 pages).

* cited by examiner

| USER ID | BODY HEIGHT | BODY WEIGHT | ABDOMINAL CIRCUMFERENCE | SYSTOLIC BLOOD PRESSURE | DIASTOLIC BLOOD PRESSURE | HEART RATE | DISEASE DEVELOPMENT |
|---|---|---|---|---|---|---|---|
| 1001 | 170 | 65 | 80 | 138 | 78 | 62 | F |
| 1002 | 170 | 65 | 90 | 145 | 78 | 80 | T |
| 1003 | 160 | 50 | 92 | 120 | 60 | 80 | F |
| ... | ... | ... | ... | ... | ... | ... | |

F I G. 2

| USER ID | BODY HEIGHT | BODY WEIGH | ABDOMINAL CIRCUMFERENCE | SYSTOLIC BLOOD PRESSURE | DIASTOLIC BLOOD PRESSURE | HEART RATE |
|---|---|---|---|---|---|---|
| 0001 | 170 | 75 | 90 | 138 | 78 | 62 |
| 0002 | 180 | 65 | 80 | 118 | 68 | 80 |
| 0003 | 160 | 80 | 92 | 148 | 89 | 80 |
| ... | ... | ... | ... | ... | ... | ... |

FIG. 3

| USER ID | SCORE | PREDICTION |
|---|---|---|
| 0001 | 0.9 | T |
| 0002 | 1.0 | T |
| 0003 | 0.5 | T |
| 0004 | 0.4 | F |
| 0005 | 0.3 | F |
| 0006 | 0.8 | T |
| 0007 | 0.6 | T |
| 0008 | 0.2 | F |
| 0009 | 0.3 | F |
| 0010 | 0.4 | F |

F I G. 5

| USER ID | SCORE | PREDICTION | WHETHER PREDICTION IS CORRECT OR WRONG |
|---------|-------|------------|----------------------------------------|
| 0001 | 0.9 | T | 0 |
| 0002 | 1.0 | T | 1 |
| 0003 | 0.5 | T | 1 |
| 0004 | 0.4 | F | 1 |
| 0005 | 0.3 | F | 1 |
| 0006 | 0.8 | T | 0 |
| 0007 | 0.6 | T | 1 |
| 0008 | 0.2 | F | 1 |
| 0009 | 0.3 | F | 1 |
| 0010 | 0.4 | F | 1 |

| USER ID | SCORE | PREDICTION | WHETHER PREDICTION IS CORRECT OR WRONG |
|---------|-------|------------|----------------------------------------|
| 0002 | 1.0 | T | 1 |
| 0001 | 0.9 | T | 0 |
| 0006 | 0.8 | T | 0 |
| 0007 | 0.6 | T | 1 |
| 0003 | 0.5 | T | 1 |
| 0004 | 0.4 | F | 1 |
| 0010 | 0.4 | F | 1 |
| 0005 | 0.3 | F | 1 |
| 0009 | 0.3 | F | 1 |
| 0008 | 0.2 | F | 1 |

TOP FIVE PIECES OF DATA

FIG. 9

| | CORRECT | WRONG | CORRECT ANSWER RATE (%) |
|---|---|---|---|
| CORRECT ANSWER RATE FOR TOP FIVE PIECES OF DATA IN ORDER OF SCORE | 3 | 2 | 60 |

FIG. 8

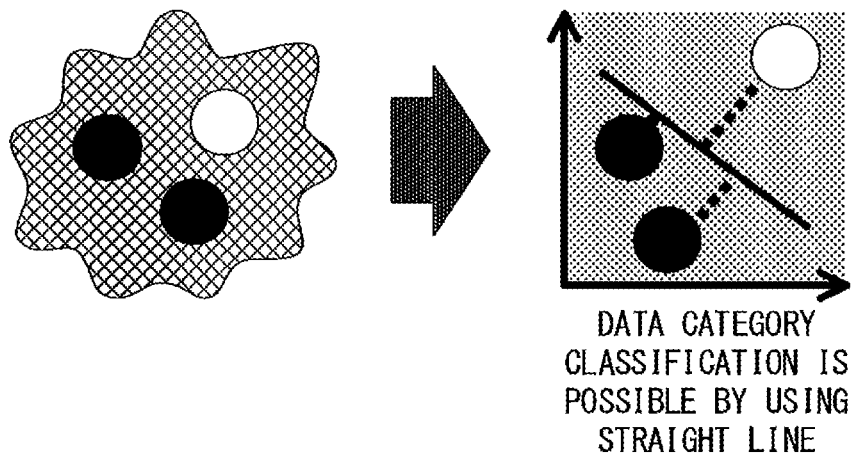
F I G. 1 0 A

| | CORRECT | WRONG | CORRECT ANSWER RATE (%) |
|---|---|---|---|
| CORRECT ANSWER RATE FOR ENTIRETY OF POPULATION FIG. 7 | 8 | 2 | 80 |

| | CORRECT ANSWER RATE FOR TOP FIVE PIECES OF DATA IN ORDER OF SCORE | |
|---|---|---|
| | CORRECT | 4 |
| | WRONG | 1 |
| | CORRECT ANSWER RATE (%) | 80 |

FIG. 18

MODEL UPDATING METHOD, MODEL UPDATING DEVICE, AND RECORDING MEDIUM

CROSS-REFERENCE TO RELATED APPLICATION

This application is a continuation application of International Application PCT/JP2013/059585 filed on Mar. 29, 2013 and designated the U.S., the entire contents of which are incorporated herein by reference.

FIELD

The embodiments discussed herein are related to a model updating method, a model updating device, and a recording medium.

BACKGROUND

In recent years, an increasing number of people suffer from lifestyle diseases, which is a major social problem. In order to prevent lifestyle diseases, it is important to perform health guidance. In health guidance which is performed by a health guidance instructor, it is necessary for the health guidance instructor to look at exam data such as physical checkup results of a subject, judge the likelihood of the subject developing lifestyle diseases in the future, and perform health guidance as necessary. In general, exam data such as physical checkup results includes numerical values of a plurality of items with respect to the body of a subject. A boundary value as a reference for judging normality or abnormality is set for each item. It is hard to find out whether or not a subject is likely to develop a medical condition which is related to an exam item by only checking whether the value of the exam data of the subject with respect to the exam item is normal or abnormal. Deterioration in health condition is determined by detecting the fact that data of a subject that was a normal value in the past is becoming closer to the boundary value or has exceeded the boundary value. As described, in regard to a health condition judgment that is made by a health guidance instructor, there is limitation in the number of predictions that one health guidance instructor can make due to time and trouble involved, and furthermore, human resources for health guidance instructors are in shortage.

For example, a method is known for estimating susceptibility to diseases in the future from exam data of a subject in consideration of hereditary data, attributes such as age, and disease history data of the subject. In the method, a method is known for estimating posterior probability distribution of the subject's susceptibility to diseases by using distribution of susceptibility to diseases that is obtained by clustering distribution of a group and gathering statistics for each clustering node.

In addition, a health guidance support system is known that computes for each specified disease the relationship between relevant exam items (screening items) and disease development and is capable of providing specific advice, for example, as to of which exam item the exam result value should be improved and how much the value should be improved in order to prevent development of the disease. In this method, statistic calculation is performed according to each data value and information on whether or not a disease was actually developed in order to find out which exam item from among a plurality of pieces of exam item data relates to development of the disease.

In order to perform data analysis (curation service), it is necessary to generate a model (health condition judgment model) in advance by using data for which the correct answer is known. Once the model is established, a customer can obtain predicted results based on the model by inputting to the model data that has been newly collected.

Patent Document 1: Japanese Laid-open Patent Publication No. 2002-109150

SUMMARY

A model updating method according to an aspect of the embodiments is a model updating method that is executed by a computer, and includes calculating a score that indicates the degree of normality or abnormality of each of a plurality of pieces of data by using each piece of data as a judgment model, predicting as a predicted condition whether each piece of data is normal or abnormal according to the score, judging whether or not the predicted condition is correct for each of the plurality of pieces of data, calculating an accuracy rate for predicted conditions of a top specified number of pieces of data in order of decreasing abnormality as indicated by the score when the plurality of pieces of data are arranged in a specified order of score, and judging whether or not it is necessary to update the judgment model according to the accuracy rate.

BRIEF DESCRIPTION OF DRAWINGS

FIG. 2 is a diagram illustrating an example of past physical checkup data in FIG. 1.

FIG. 3 is a diagram illustrating an example of new physical checkup data in FIG. 1.

FIG. 5 is a diagram illustrating examples of predicted results that are outputs from a predicting unit of the health condition judgment model updating device.

FIG. 7 is a diagram illustrating examples of judgment results on predicted results in the health condition judgment model updating device.

FIG. 8 is a diagram illustrating an example for arranging judgment results on predicted results in descending order of score in the health condition judgment model updating device.

FIG. 9 is a diagram illustrating the accuracy rate for a top five pieces of data in the health condition judgment model updating device.

FIG. 10A is a diagram illustrating an example of classification in machine learning.

FIG. 15 is a diagram illustrating an accuracy rate for predicted results in a comparative example.

FIG. 19 is a diagram illustrating the accuracy rate for the top five pieces of data in the health condition judgment model updating device of the modification.

DESCRIPTION OF EMBODIMENTS

Figure 1:
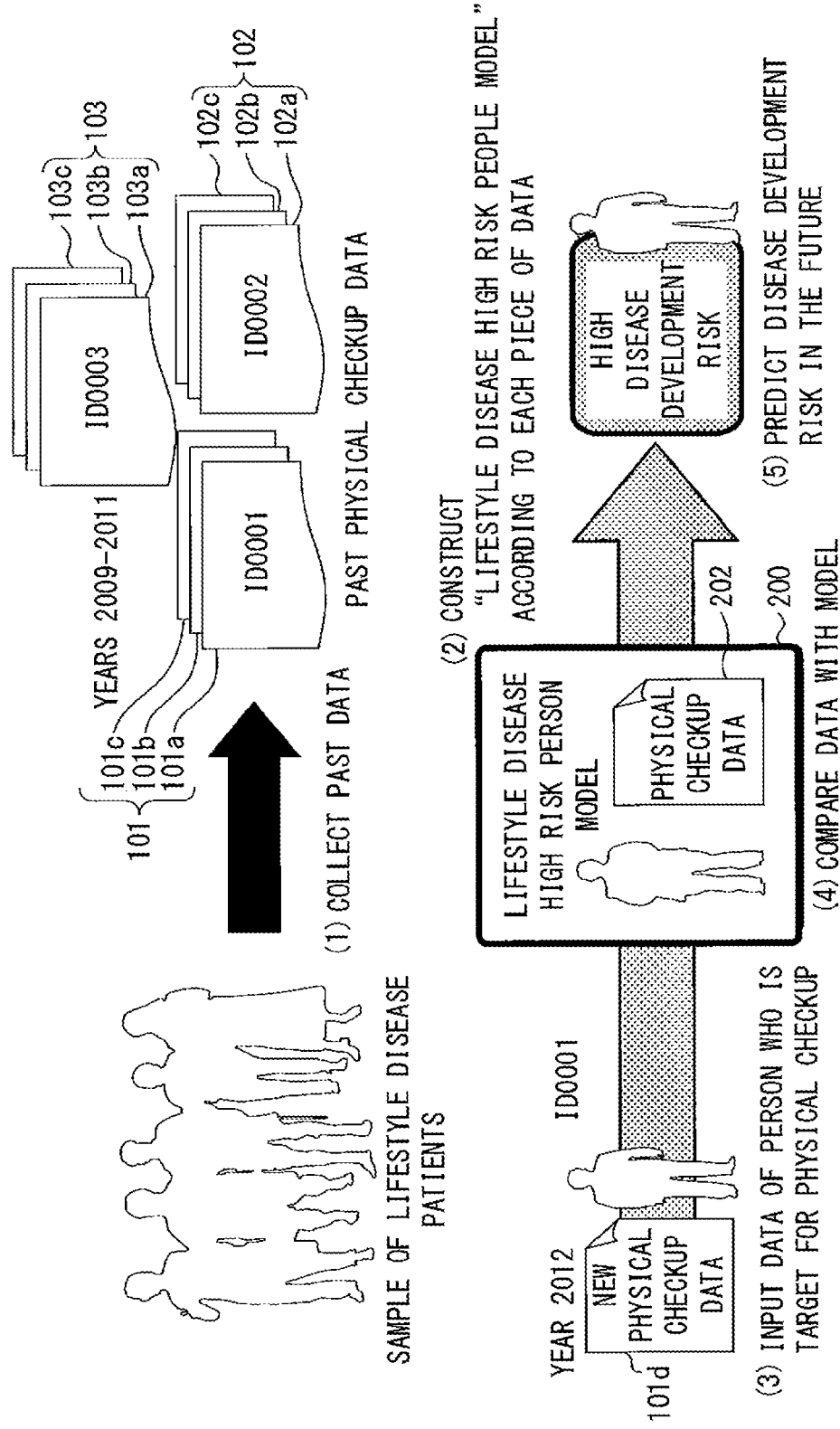
FIG. 1 is a diagram illustrating an example of a situation to which a health condition judgment model updating device and a health condition judgment model updating method of an embodiment are applied.

After the model is created, it is not possible to use the model forever. In a case in which there is a major change in the trends of input data and analysis targets themselves, there is a problem in which it is highly likely that the original model will not maintain a high accuracy rate.

Therefore, in one aspect, embodiments aim to provide a model updating method, device and program for judging whether or not it is necessary to update (recreate) a model that has been established.

The embodiments of the present invention will be described with reference to drawings.

Hereinafter, as examples of the model updating device and the model updating method, a health condition judgment model updating device and a health condition judgment model updating method will be described, respectively. However, in the following description, the model updating device and the model updating method are not limited to the health condition judgment model updating device and the health condition judgment model updating method, and are applicable to any device and method for improving and maintaining prediction accuracy by making a judgment on whether or not it is necessary to update a model that predicts a condition from data. The judgment is made by using a top specified number of pieces of data in descending order of score that is derived from each piece of data from among a population that is composed of all the pieces of data.

"Model" may have a function of predicting a condition (predicted condition) from data. Here, "data" may be, for example, physical checkup data of a subject. In this case, "condition" may be a presence or absence of likelihood to develop a disease. In another example, "data" may be maintenance inspection data that relates to safety of a structure. In this case, "condition" may be whether or not the structure is safe.

When data includes values of a plurality of items, "Score" may be a scalar quantity that servers as an index of "condition" that is obtained from the values of the plurality of items.

"Health condition judgment model" may have a function of outputting information indicating that an exam data value of an exam item of a subject in a physical checkup is "normal" or "abnormal" by inputting the exam data value. The health condition judgment model may be referred to as a prediction model, a judgment model, or simply a model. The model may be a mathematical model or a computing model such as a neural network and a support vector machine for realizing an algorithm to which supervised learning is applicable. That is, the health condition judgment model judges the health condition of a subject from physical checkup results (data) by using past physical checkup results and records of an actual health condition of the subject. The health condition may be normal or abnormal with respect to a physical checkup exam item in consideration of characteristics of a subject. For example, in the health condition judgment model, when a health checkup result of a subject is input, information indicating whether health checkup data with respect to an exam item is normal or abnormal may be output. The model may include a parameter, and the parameter may be calculated by using learned data.

Here, "Constructing a model" may be setting by using a plurality of pieces of data a structure of a model (type of mathematical expression, etc.) and a parameter for realizing a function that the model is intended to have. In the case in which the model is a health condition judgment model, the model may be constructed by using physical checkup result data of a plurality of subjects. In the case in which the model is a mathematical model or a computing model for realizing the algorithm to which supervised learning is applicable, "constructing a model" may mean performing supervised learning and may include setting for a specified group a threshold (also referred to as judgment value) for whether data is normal or abnormal. For example, a boundary value that has been determined in an international organization or an academic society, etc. may be verified by using actual exam data and the boundary value may be changed as necessary so that correlation increases between exam data values and disease development or high susceptibility to a disease. In this case, exam data may be used as data (learned data) for supervised learning of the model. That is, when exam data is input, the model outputs information indicating that the exam data value is "normal" or "abnormal". Then, when the model includes a structure and a parameter, the structure and the parameter are decided by using the actual exam data and presence or absence of development of a disease so that output prediction accuracy of the model becomes high.

Here, "a data value is abnormal" may mean that the condition that is predicted from the data (predicted condition) is not preferable. For example, "an exam data value is abnormal" may mean that it is possible to argue from a statistical or medical point of view that the exam data value is relevant to development of the disease that relates to the exam item in question. In addition, "an exam data value is abnormal" may mean that it is possible to argue from a statistical or medical point of view that the exam data value is relevant to susceptibility to the disease that is related to the exam item in question. The fact that a data value is abnormal may mean that the risk of development of a disease in the future is high. A high risk of development of a disease in the future may be referred to as simply a presence of likelihood of development of a disease. Absence of likelihood of development of a disease development may mean that there is no presence of likelihood of development of a disease.

When determining whether or not to update the health condition judgment model, the health condition judgment model updating device and the health condition judgment model updating method that will be disclosed hereinafter calculates not an accuracy rate for the entirety of a population but for n pieces of data that are a portion of the data of the population, and judges whether or not to update the model according to the calculated accuracy rate. Here, n pieces of data may include a top n pieces of data that are ranked according to prediction degree of predicted results of the entirety of the population. From among n pieces of data, pieces of data of people for whom health guidance has been performed (referred to as data for which measures have been taken) may be excluded from accuracy rate calculation targets. Here, the value of n may be a specified percentage of the total number of pieces of data, for example, 5% or 10%, or may be an absolute number such as 200. It is preferable that the value of n be related to the number of subjects for whom it is possible to actually perform guidance.

By using such a health condition judgment model updating device and such a health condition judgment model updating method, it is possible to decide on a model updating timing so that the accuracy rate may be improved and maintained for some meaningful prediction targets in the population.

"Health condition judgment" (also referred to simply as health judgment) may mean judging whether a subject has developed a disease that is related to an exam item or has a high susceptibility to the disease according to the exam data value of the exam item of the subject who had a physical checkup. Examples of the disease may include lifestyle diseases such as diabetes, metabolic syndrome, abnormal glucose tolerance, hypertension, and hyperlipidemia. Exam items may include age, body mass index (BMI), abdominal circumference, blood glucose level, Γ-GTP (γ-glutamyl transpeptidase), blood pressure, cholesterol, insulin resistance index, plasma glucose, neutral fat, hepatic function (AST, IU/L), hepatic function (ALT, IU/L), adiponectin, glycoalbumin, free fatty acid, and insulin, etc.

The health condition judgment model updating device may be a general-purpose computer or a dedicated circuit. In addition, the health condition judgment model updating device may be configured by incorporating a dedicated circuit into a general-purpose computer.

FIG. 1 is a diagram illustrating an example of a situation to which a health condition judgment model updating device and a health condition judgment model updating method of the embodiment are applied.

In FIG. 1, lifestyle disease patients are targets. Each lifestyle disease patient is identified by means of an ID.

Then, past physical checkup data is prepared for each lifestyle disease patient. For example, as illustrated in FIG. 1, for a lifestyle disease patient who is numbered ID 0001, data 101a in 2009, data 101b in 2010, and data 101c in 2011 (which may be collectively referred to by using reference sign 101) is prepared. For a lifestyle disease patient who is numbered ID 0002, data 102a in 2009, data 102b in 2010, and data 102c in 2011 (which may be collectively referred to by using reference sign 102) is prepared. For a lifestyle disease patient who is numbered ID 0003, data 103a in 2009, data 103b in 2010, and data 103c in 2011 (which may be collectively referred to by using reference sign 103) is prepared.

Lifestyle disease high-risk person model 200 is constructed as a health condition judgment model by using as learned data the above past physical checkup data.

FIG. 2 is a diagram illustrating an example of past physical checkup data in FIG. 1. In FIG. 2, data of each subject (user) includes body height, body weight, abdominal circumference, systolic blood pressure, diastolic blood pressure, heart rate, and a presence or absence of development of a disease (True (T) or False (F)). FIG. 2 may be a table that is obtained by compiling subjects' data 101c, 102c, and 103c in 2011.

After the model has been constructed, physical checkup data 101d of people who are targets for physical checkups, that is, candidates for lifestyle diseases (hereinafter may be referred to simply as data when no misunderstandings occur) is input to the health condition judgment model (lifestyle disease high-risk person model 200).

FIG. 3 is a diagram illustrating an example of new physical checkup data 101d in FIG. 1. In FIG. 3, data on each subject (user) includes body height, body weight, abdominal circumference, systolic blood pressure, diastolic blood pressure, and heart rate. FIG. 3 may be a table that is obtained by compiling subjects' data 101d, 102d, and 103d, etc. in 2012.

In the model 200, it is judged whether exam item data of the physical checkup data 101d is normal or abnormal. Here, it is assumed that an abnormal data value indicates a high risk of development of a disease in the future, that is, a presence of likelihood of development of a disease.

After a model is created, it is not possible to use the model forever. In a case in which there is a major change in the trends of input data and analysis targets themselves, it is highly likely that the original model will not be able to maintain a high accuracy rate. For example, it is not possible to obtain a high accuracy rate in a case of making a diabetes development prediction for company B where workers take shifts and often work a night shift by using the model for company A where workers mainly do office work in the daytime, because characteristics of members are different between company A and company B. In addition, even though disease development predictions are made for the same company A, the accuracy rate might deteriorate over time in the case of continuously using the same model, because of turnover each year.

Therefore, it is necessary to appropriately check whether a model that has been established is required to be updated (that is, to be recreated).

For example, under the assumption that diabetes development predictions are made for 20,000 people and correct predictions are made for all of the 20,000 people, health guidance instructors will perform some kind of guidance for the people whose data has turned out to be "abnormal", that is, who may "develop the disease in the future". If there were enough health guidance instructors, it would be possible to cope with all the people who are judged to be likely to "develop disease in the future" (judged to have a presence of likelihood of development of a disease); however, since there are not enough health guidance instructors in reality, guidance is performed mainly for "people who are highly likely to develop the disease" among people who are judged to be likely to "develop the disease in the future".

Eventually, even though it is possible to correctly predict a presence or absence of a likelihood of development of a disease, since the number of people for whom it is possible to perform guidance is limited, it is meaningless to make predictions for a greater number of people than it is possible to perform guidance for. (As a matter of fact, the problem is that medical costs for "people who are highly likely to develop diseases" are enormous, and medical costs for the other people are not so high, considering the tremendous medical costs that a company pays for its corporate health insurance policy.) It is possible to take the view that since it is possible to cope with only 100 people even though it is possible to make predictions for 20,000 people, prediction accuracy is not important for the rest of the 19,900 people.

When determining whether or not to update the health state judgment model, the health condition judgment model updating device and the health condition judgment model updating method of the embodiment that will be hereinafter described calculate not an accuracy rate for the entirety of a population that is composed of pieces of data of subjects who had medical checkups but an accuracy rate for a specified number of pieces of data that are a portion of the data of the population, and judge whether or not to update the model according to the calculated accuracy rate.

<Health Condition Judgment Model Updating Device>

Figure 4:
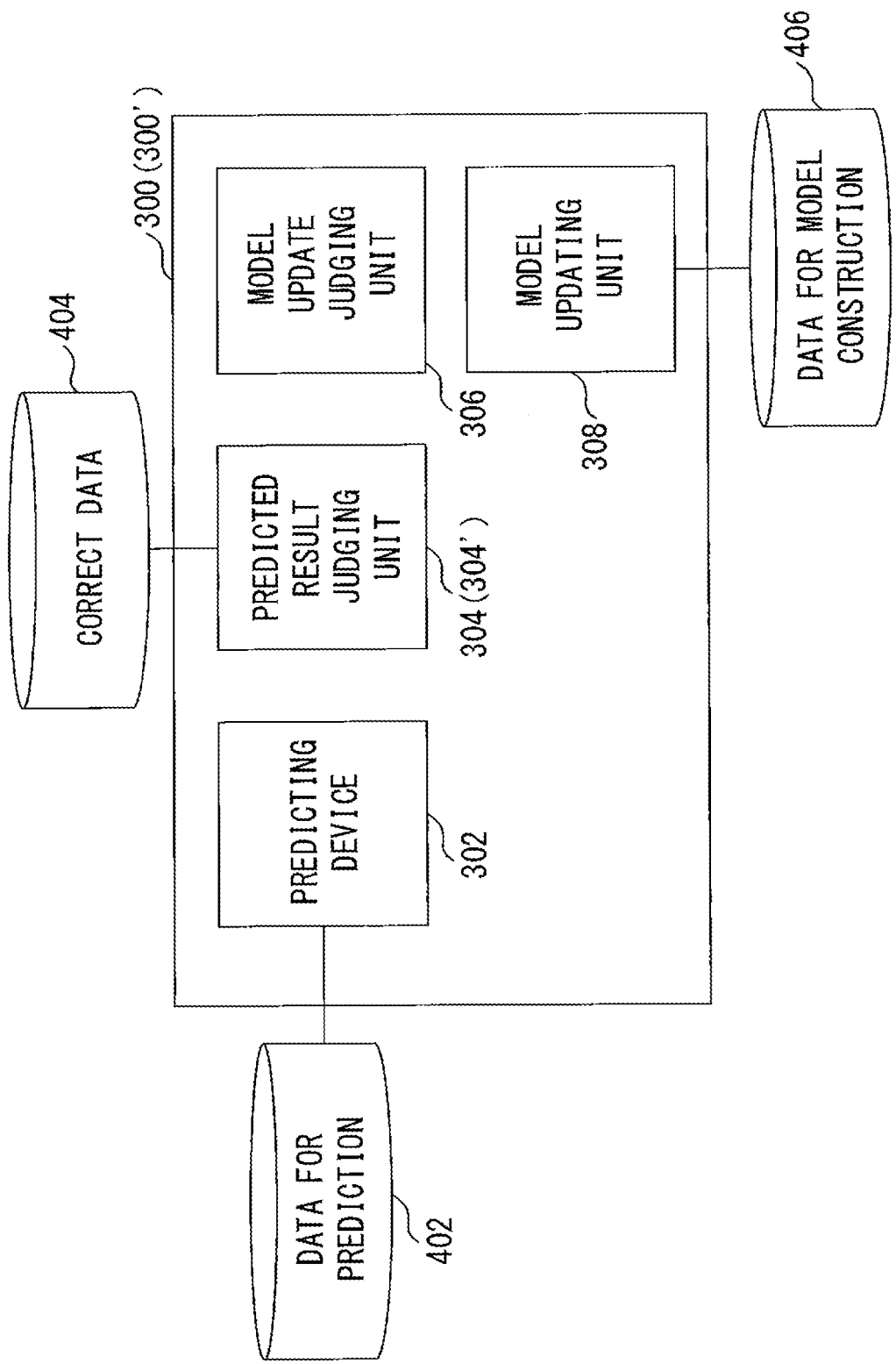
FIG. 4 is an example of a functional block diagram of the health condition judgment model updating device.

FIG. 4 is an example of a functional block diagram of a health condition judgment model updating device 300.

The health condition judgment model updating device 300 is configured to refer as necessary to data for prediction 402, correct data 404, and data for model construction 406. A health condition judgment model updating device 300' includes a predicting unit 302, a predicted result judging unit 304', a model update judging unit 306, and a model updating unit 308. In this example, the health condition judgment model updating device 300 will be described.

The health condition judgment model updating device 300 judges whether or not it is necessary to update a model according to the following procedures.

First, a disease development information portion is separated from past physical checkup results, and data for prediction 402, which is physical checkup result data from which disease development information has been separated, is prepared. The separated disease development information portion is referred to as correct data 404. Next, a prediction on development of a disease is made according to data for prediction 402 by using the health condition judgment model. Then, results of predictions are compared with correct data 404 and the correct answer rate is calculated. When the correct answer rate satisfies the reference value, updating will not be performed. When the correct answer rate is below the reference value, updating will be performed.

Data for prediction 402, an example of which is illustrated in FIG. 2, may be past physical checkup exam data portions of past physical checkup data 101, 102, and 103 that include past physical checkup exam data for each subject and presence or absence of development of a disease. In the example in FIG. 2, correct data 404 is a column for a presence or absence of development of a disease.

The health condition judgment model updating device 300 includes the predicting unit 302 that makes a prediction, a predicted result judging unit 304, and the model updating unit 308.

The predicting unit 302 calculates a score that indicates the degree of normality or abnormality of each of a plurality of pieces data by using each of the pieces of data as a judgment model. The predicting unit 302 predicts as a predicted condition whether each piece of data is normal or abnormal according to score.

The predicted result judging unit 304 judges for each of the plurality of pieces of data whether or not a predicted condition that has been predicted by the predicting unit 302 is correct.

The model update judging unit 306 calculates the accuracy rate for predicted conditions for the top specified number of pieces of data in order of decreasing abnormality as indicated by the score when a plurality of pieces of data are arranged in a specified order of score. The model update judging unit 306 judges according to the accuracy rate whether or not it is necessary to update the judgment model.

When the model update judging unit 306 judges that it is necessary to update the judgment model, the model updating unit 308 updates the judgment model so as to improve the accuracy rate by changing at least one of the parameter that is included in the model and learned data that is used to decide on the parameter.

Data for prediction 402 is input to the predicting unit 302. Then, the predicting unit 302 calculates a "score" that indicates the degree of normality or abnormality of data for prediction 402 by using the health condition judgment model. Here, "score" is a scalar quantity that is obtained from data for prediction 402 and is related to physical checkup exam data of a subject. "Score" is a quantity that is related to whether data for prediction 402 is normal or abnormal. For example, the score may be represented by a number from 0 to 1. In addition, for example, the score may be represented by a larger value as the degree of abnormality increases.

In regard to a prediction algorithm, a prediction algorithm that uses probability and statistics, a prediction algorithm that uses multiple regression, and a prediction algorithm that uses machine learning are possible. As a technique for machine learning, a support vector machine (SVM) may be used.

The support vector machine (SVM) is a classifier that performs supervised learning, and is one of a group of techniques that perform classification most accurately in a classification problem. SVM makes a prediction in two stages, a "learning phase" and a "prediction phase". In the "learning phase", SVM learns characteristics by using training data and constructs a "prediction phase", and in the "prediction phase", SVM makes a prediction by obtaining new data. Update timing in the health condition judgment model updating device 300 indicates a timing at which the "learning phase" is performed again. In the prediction that is made by SVM, the distance from a plane that separates prediction target data (referred to as separating hyperplane) is obtained.

FIG. 10A is a diagram illustrating an example of classification in machine learning. FIG. 10A illustrates a case of classifying three pieces of data. The pieces of data are arranged in a parameter space, and the pieces of data may be classified according to distance from each piece of data to a straight line in the parameter space. In this case, the straight line in the parameter space may be referred to as a separating hyperplane. The distance from a piece of data to the straight line in the parameter space is defined as a "score".

Figure 10B:
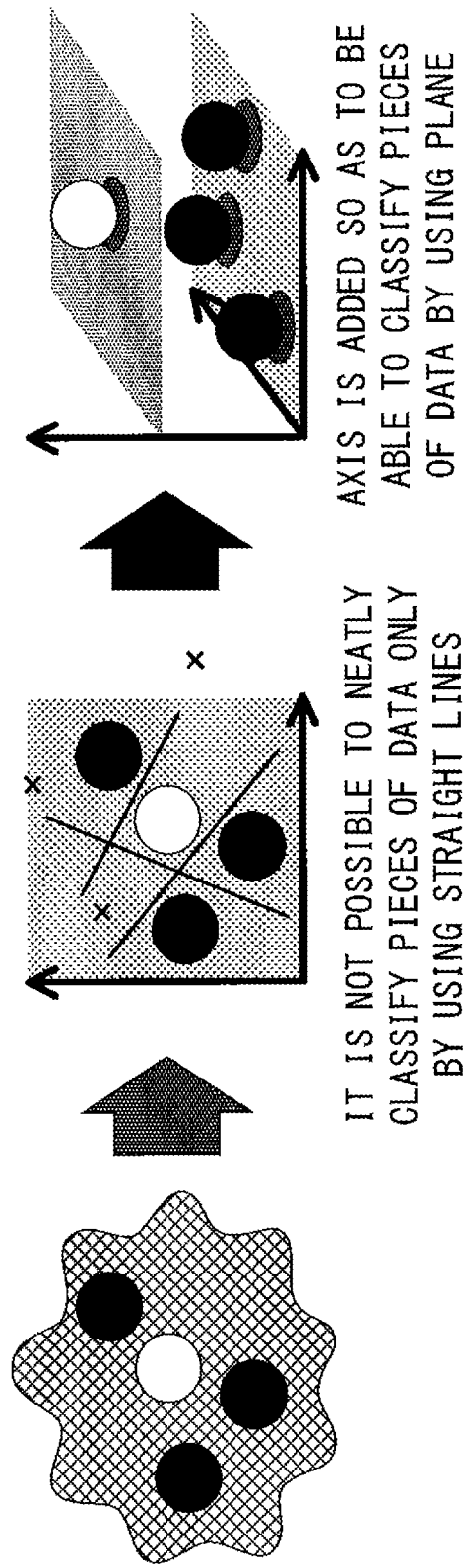
FIG. 10B is a diagram illustrating another example of classification in machine learning.

FIG. 10B is a diagram illustrating another example of classification in machine learning. FIG. 10B illustrates a case of classifying four pieces of data. The pieces of data are arranged in a parameter space, and it is not possible to neatly classify the pieces of data by using only straight lines. Therefore, dimensions of the parameter space are increased (an axis is added), and the pieces of data are classified by using a plane. That is, the distance from a piece of data to a hyperplane is defined as a "score". In general, as the distance from a separating hyperplane becomes longer, the probability that the prediction is correct will increase.

FIG. 5 is a diagram illustrating examples of predicted results that are outputs from the predicting unit 302. The examples of predicted results that are illustrated in FIG. 5 include user ID, score, and the result of a prediction of a presence or absence of development of a disease (True (T) or False (F)). The presence or absence of development of a disease indicates a result that is obtained by judging whether data is normal or abnormal according to score. It is assumed that when the score is greater than a specified value, it is judged to indicate a presence of likelihood of development of a disease (True (T)), and otherwise it is judged to indicate an absence of likelihood of development of a disease (False (F)). A presence or absence of likelihood of development of a disease may be referred to as a predicted condition.

As described, the predicting unit 302 calculates a score that indicates the degree of normality or abnormality of each piece of a plurality of data that correspond to a plurality of subjects respectively by using each piece of the data as the judgment model, and predicts as a predicted condition whether each piece of the data is normal or abnormal according to the score.

The predicted result judging unit 304 compares the result that has been predicted by the predicting unit 302 and correct data 404 with each other and calculates an accuracy rate.

Figure 6:
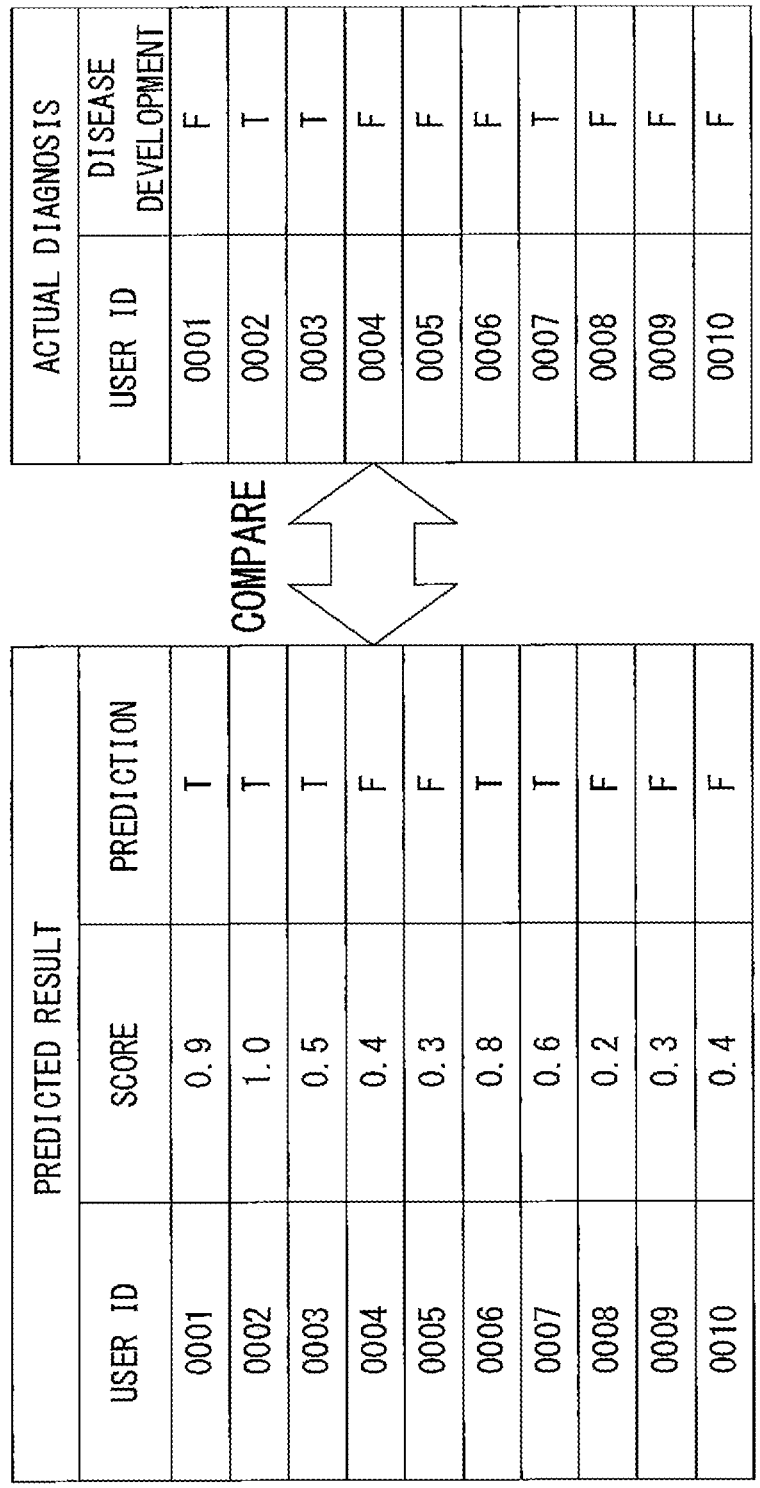
FIG. 6 is a diagram illustrating a state in which predicted results are compared with actual diagnoses in the health condition judgment model updating device.

FIG. 6 is a diagram illustrating a state in which predicted results are compared with actual diagnoses in the health condition judgment model updating device. For example, focusing on the subject with user ID 0001, the score in the predicting unit 302 was "0.9" and the presence of likelihood of development of a disease (True (T)) was predicted in the predicted result. However, the subject did not actually develop a disease, and the result was an absence of development of the disease (False (F)). In this case, the prediction on the subject with user ID 0001 is referred to as wrong. A wrong prediction may be indicated by a symbol "0". A prediction that is not wrong, that is, a correct prediction, may be indicated by a symbol "1". The predicted result judging unit 304 compares the predicted result and the actual diagnosis with each other for each user, and outputs, for example, a result that is illustrated in FIG. 7.

FIG. 7 is a diagram illustrating examples of judgment results on predicted results in the predicted result judging unit 304 of the health condition judgment model updating device 300. Since the prediction on the subject with user ID 0001 did not come true, the prediction is wrong, that is, the correctness of the prediction is "0".

As described, the predicted result judging unit 304 judges whether or not the predicted condition that was predicted by the predicting unit 302 is correct for each of the plurality of pieces of data of a plurality of subjects.

The model update judging unit 306 judges whether or not to update the model according to a judgment result on the predicted result in the predicted result judging unit 304. At that time, when judging whether or not to update the health condition judgment model, not the accuracy rate for the entirety of the population but the accuracy rate for only a specified number of pieces of data that are a portion of the the population is calculated, and whether or not to update the model is judged according to the calculated accuracy rate. For example, the model may be updated in the case in which the accuracy rate is below a specified judgment reference value. An arbitrary accuracy rate such as 80%, 60%, or 90% may be set as the judgment reference value.

FIG. 8 is a diagram illustrating an example for arranging judgment results on predicted results in descending order of score in the predicted result judging unit 304 of the health condition judgment model updating device 300.

The predicted result judging unit 304 calculates an accuracy rate for the top five pieces of data in descending order of score. FIG. 9 is a diagram illustrating the accuracy rate for the top five pieces of data in the health condition judgment model updating device. In the case of FIG. 8, the top five pieces of data in descending order of score are five pieces of data that correspond to user IDs "0002", "0001", "0006", "0007", and "0003", respectively. The accuracy rate that is calculated from the pieces of data is 60%, as illustrated in FIG. 9. Referring to the column "whether prediction is correct or wrong", the accuracy rate is 60%.

Here, when it is assumed that the model is updated in the case in which the correct answer rate is below 60%, that is, in the case in which the judgment reference value is 60%, it is judged to update the model in the case of FIG. 9.

A specified number (of pieces of data that are selected from some of the pieces of data of the population) may be referred to as a "reference number".

The reference number is determined, for example, in the following manner.

In the case of lifestyle disease prediction, even though predictions have been made for all the pieces of data, the number of people for whom it is possible to actually perform health guidance is limited. Therefore, it is more preferable to correctly predict people at whom health guidance is targeted than to make a correct prediction as a whole. In view of that, the health condition judgment model updating device 300 judges model accuracy (for example, an accuracy rate) not according to the prediction accuracy for the entirety but according to the prediction value of data set N that has certain characteristics. As data characteristics, the following characteristics are possible.

(C1) Top n Scores

As the top n scores, it is possible to use a percentage, such as the top 10%. For example, it may be judged to update the model in a case in which the accuracy for the top 100 scores (for example, the accuracy rate) is below 90%.

(C2) Narrowing-down According to Attribute

For example, an accuracy rate may be calculated by using data of the top 100 people whose BMI is greater than or equal to 25 and data of the top 100 people whose age is older than or equal to 40.

(C3) Combination of a Plurality of Attributes

A standard may be set by combining a plurality of attributes, for example, the top 100 people whose age is older than or equal to 60 and whose BMI is greater than or equal to 25, and the top 100 people in weight increase rate from the previous year whose age is greater than or equal to 40.

As described, the model update judging unit 306 calculates the accuracy rate for predicted conditions of some of the top specified number of pieces of data in descending order of score from among a plurality of pieces of data that correspond to a plurality of subjects, and judges according to the accuracy rate whether or not it is necessary to update the judgment model. When the accuracy rate is calculated, the accuracy rate for the predicted conditions of some of the plurality of pieces of data that have scores greater than or equal to a specified value from among a plurality of pieces of data may be calculated.

When the model update judging unit 306 determines to update the model, the model updating unit 308 updates the health condition judgment model. Then, the updated model is set to be used in the predicting unit 302.

As a specific method for a model update, the following methods are possible.

(M1) Reconstruct the model by changing various parameters that were used when the model was constructed For example, models are reconstructed by changing the type of formula and various parameters to be used, accuracies of the reconstructed models are compared with each other, and the most appropriate parameter is calculated.

(M2) Reconstruct the model by changing learned data

For example, data that is different from the data that was used for learning before is prepared, and the model is reconstructed. Learning may be performed by using data that has been accumulated after the time point when learning was performed last time.

(M3) Reconstruct the model by changing various parameters and learned data

The model is reconstructed by simultaneously executing (M1) and (M2) above.

When the update judging unit 306 judges that it is necessary to update the model, the model updating unit 308 updates the model so that the accuracy rate will be improved by changing at least one of the parameter and the learned data of the model.

Use of the health condition judgment model updating device 300 that is configured as above makes it possible to maintain health condition prediction accuracy by judging whether or not it is necessary to update a health condition judgment model that predicts health conditions of subjects by using pieces of data of as many of the subjects as the number of subjects for whom it is possible to perform health guidance from among the population that is composed of pieces of data of the subjects who had medical checkups.

Figure 11:
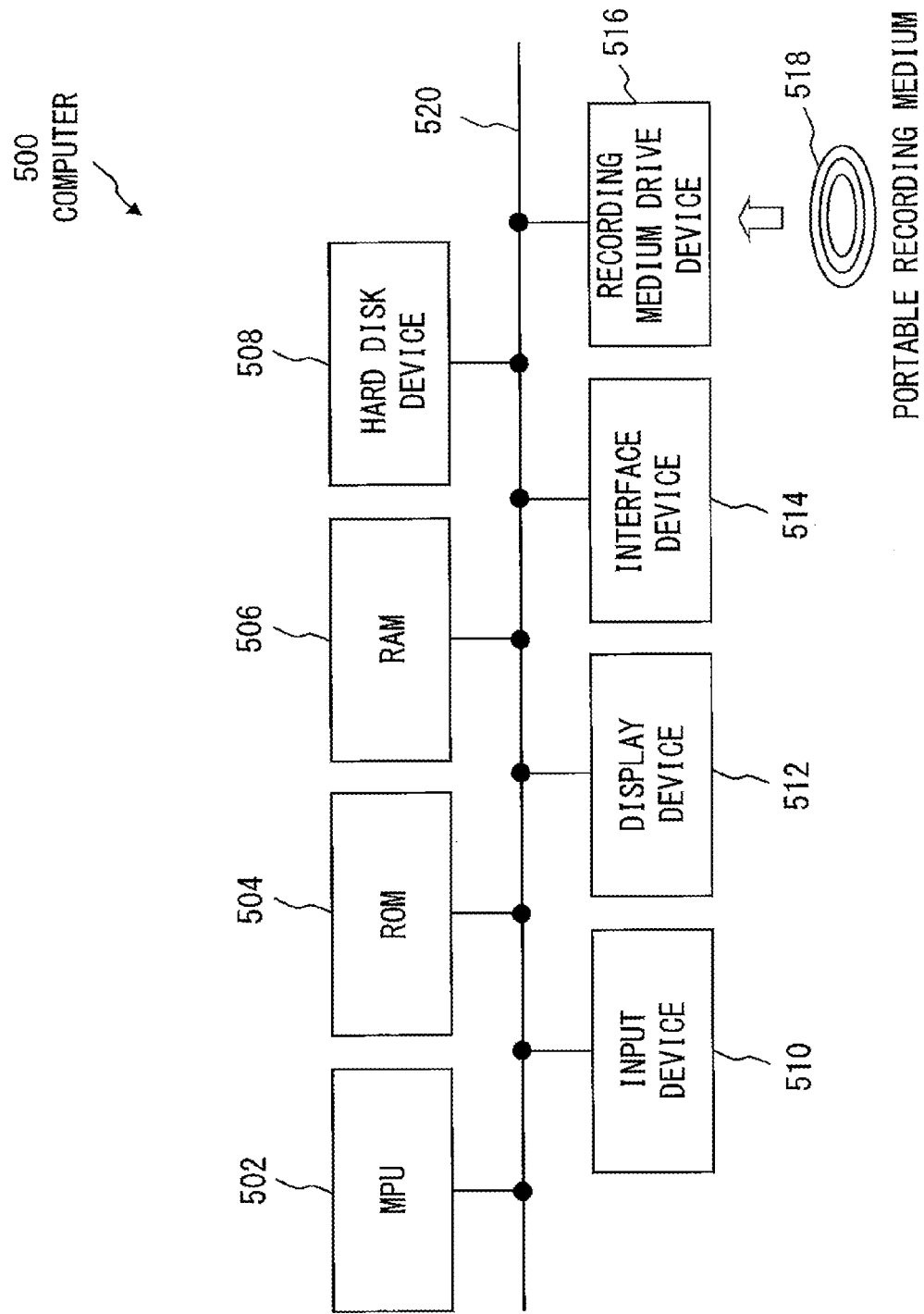
FIG. 11 is a diagram illustrating an example of the configuration of the health condition judgment model updating device of the embodiment.

FIG. 11 is a diagram illustrating an example of the configuration of the health condition judgment model updating device 300 of the embodiment. The health condition judgment model updating device may be realized as a general-purpose computer 500.

The computer 500 includes an MPU 502, a ROM 504, a RAM 506, a hard disk device 508, an input device 510, a display device 512, an interface device 514, and a recording medium drive device 516. Note that these constituents are connected with one another via a bus line 520, and may transmit and receive various pieces of data under control of the MPU 502.

The MPU (Micro Processing Unit) 502 is a processor that controls operations of the entirety of the computer 500, and functions as a control processing unit of the computer 500.

The ROM (Read Only Memory) 504 is a read-only semiconductor memory in which a specified basic control program is recorded in advance. The MPU 502 may control operations of each constituent of the computer 500 by reading and executing the basic control program at start-up of the computer 500.

The RAM (Random Access Memory) 506 is an always writable and readable semiconductor memory that the MPU 502 uses as a working storage area as necessary when executing various control programs.

The hard disk device 508 is a storage device that stores various control programs that are executed by the MPU 502 and various pieces of data. The MPU 502 may perform various control processes that will be described later by reading and executing a specified control program that is stored in the hard disk device 508.

The input device 510 is for example a mouse device or a keyboard device. When the input device 510 is operated by a user of the system in FIG. 6, the input device 510 acquires input of various pieces of information that are associated with the operation content, and transmits to the MPU 502 the acquired input information.

The display device 512 is, for example, a liquid crystal display and displays various text and images according to display data that has been transmitted from the MPU 502.

The interface device 514 manages transmission and reception of the various information between itself and various apparatuses that are connected to the computer 500.

The recording medium drive device 516 reads various control programs and pieces of data that are stored in a portable recording medium 518. The MPU 502 may perform various control processes that will be described later by reading and executing via the recording medium drive device 516 a specified control program that is recorded in the portable recording medium 518. Note that examples of the portable recording medium 518 include a flash memory that is provided with a USB (Universal Serial Bus)-standard connector, a CD-ROM (Compact Disc Read Only Memory), and a DVD-ROM (Digital Versatile Disc Read Only Memory).

In order to configure the health condition judgment model updating device by using the computer 500 as described above, for example, a control program is created that causes the MPU 502 to perform processes in each of the above processing units. The created control program is stored in advance in the hard disk device 508 or the portable recording medium 518. Then, specified instructions are given to the MPU 502 and the MPU 502 is caused to read and execute the control program. Thus, the functions that the health condition judgment model updating device has are provided by the MPU 502.

<Model Update Judging Method>

The health condition judgment model updating method will be described with reference to FIGS. 12-14.

In a case in which the device is a general-purpose computer as illustrated in FIG. 11, the following description defines the control program that performs the process that will be described in the following description. That is, the following is also a description of the control program that causes the general-purpose computer to perform the process that will be described below.

When the process is started, first, in S102, the predicting unit 302 of the health condition judgment model updating device 300 acquires N pieces of physical checkup information that includes disease development data. Here, physical checkup information that includes disease development data may include information on a user as illustrated in FIG. 2 such as body height, body weight, abdominal circumference, systolic blood pressure, diastolic blood pressure, heart rate, and a presence or absence of development of a disease (True (T) or False (F)). Then, the process proceeds to S104.

In S104, the predicting unit 302 of the health condition judgment model updating device 300 calculates a score according to physical checkup information from which disease development data has been separated, and predicts a presence or absence of likelihood of development of a disease (predicted condition). The predicted condition is also a predicted result. Then, the process proceeds to S106.

In S106, the predicting unit 302 of the health condition judgment model updating device 300 sorts predicted results in descending order of score. Examples of the predicted results that are sorted in descending order of score are illustrated in FIG. 8. Then, the process proceeds to S108.

In S108, the predicting unit 302 of the health condition judgment model updating device 300 acquires the top n (reference number) predicted results from among the sorted predicted results. FIG. 8 illustrates an example of acquiring the top five predicted results. Then, the process proceeds to S110.

In S110, the predicted result judging unit 304 of the health condition judgment model updating device 300 resets dummy variables i, T, and F so that i=1, and T=F=0. Here, dummy variables i, T, and F are integers. Dummy variable i is used for specifying one of the predicted results. Dummy variable T is used for indicating the number of predicted results that have turned out to be correct. Dummy variable F is used for indicating the number of predicted results that have turned out to be wrong. Then, the process proceeds to S112.

In S112, the predicted result judging unit 304 of the health condition judgment model updating device 300 increments the value of dummy variable i by one. Then, the process proceeds to S114.

In S114, the predicted result judging unit 304 of the health condition judgment model updating device 300 judges whether or not the i-th predicted result is correct. When the judgment result is "Yes", that is, when the i-th predicted result is correct, the process proceeds to S116. When the judgment result is "No", that is, when the i-th predicted result is wrong, the process proceeds to S118.

In S116, the predicted result judging unit 304 of the health condition judgment model updating device 300 increments the value of dummy variable T by one. Then, the process proceeds to S120.

In S118, the predicted result judging unit 304 of the health condition judgment model updating device 300 increments the value of dummy variable F by one. Then, the process proceeds to S120.

In S120, the predicted result judging unit 304 of the health condition judgment model updating device 300 judges whether or not dummy variable i is greater than or equal to reference number n. When the judgment result is "Yes", that is, when dummy variable i is greater than or equal to reference number n, the process proceeds to S122. When the judgment result is "No", that is, when dummy variable i is not greater than or equal to reference number n, the process returns to S112.

In addition, in S120, the predicted result judging unit 304 of the health condition judgment model updating device 300 may calculate the accuracy rate T/n(=T/(T+F)) after the result has been judged to be "Yes", that is, after dummy variable i has been judged to be greater than or equal to reference number n.

In S122, the model update judging unit 306 of the health condition judgment model updating device 300 judges whether or not the accuracy rate T/n (=T/(T+F)) is greater than the judgment reference value. When the judgment result is "Yes", that is, when the accuracy rate T/n is greater than the judgment reference number, the process is terminated. When the judgment result is "No", that is, when the accuracy rate T/n is not greater than the judgment reference value, the process proceeds to S124.

In S124, the model updating unit 308 of the health condition judgment model updating device 300 performs a model updating process. The model updating process will be described with reference to FIG. 13.

Figure 13:
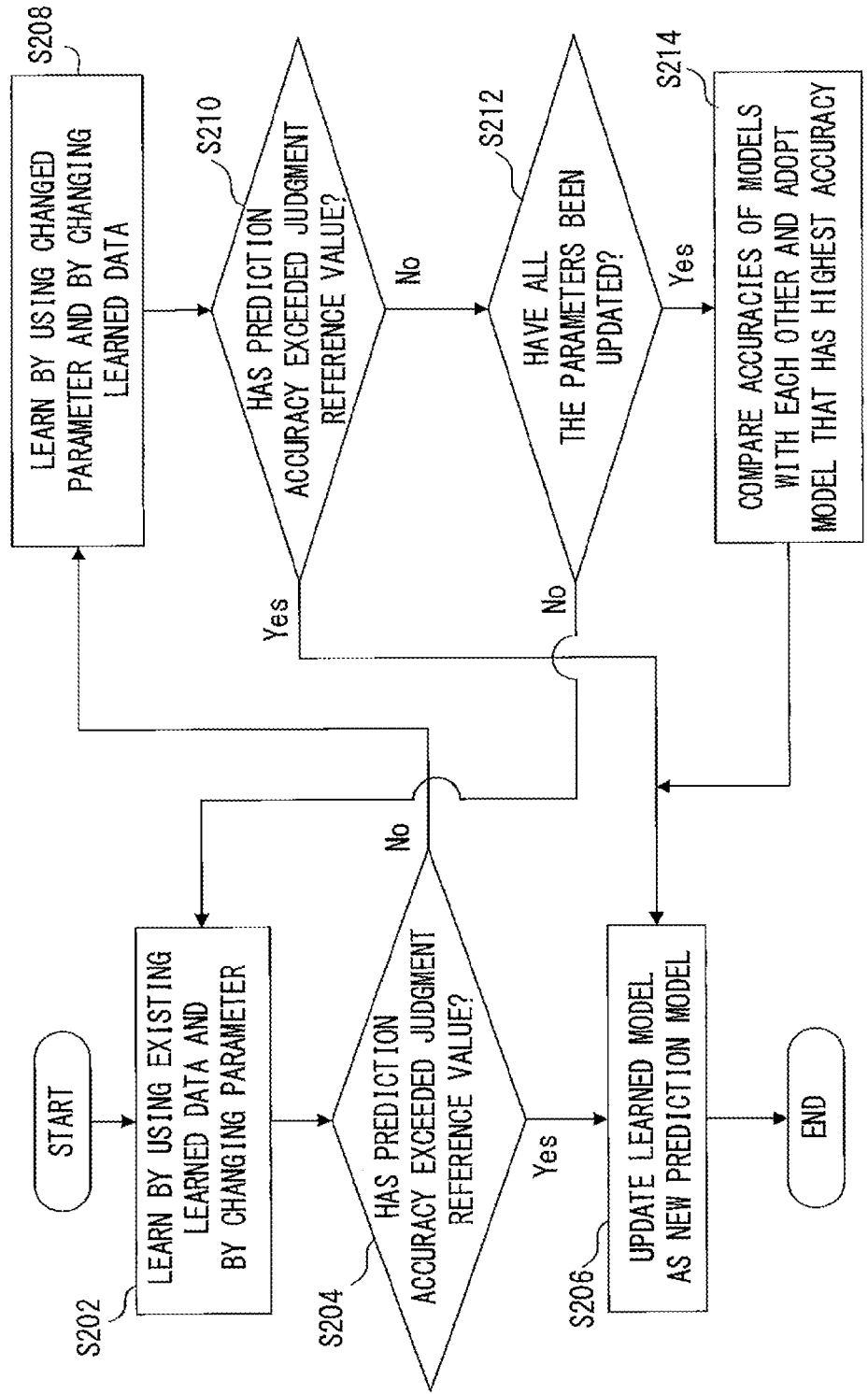
FIG. 13 is a flowchart illustrating an example of a model updating process flow in the health condition judgment model updating method.

FIG. 13 is a flowchart illustrating an example of a model updating process flow in the health condition judgment model updating method.

When the process is started, in S202, the model updating unit 308 of the health condition judgment model updating device 300 learns by using existing learned data and by changing a parameter. That is, in the same manner as the above (M1) method, the model is reconstructed by changing one of the parameters of the model while using the existing learned data. Here, it is assumed that "parameter" of the health condition judgment model includes the type of formula that is used in the model and a parameter that is included in a mathematical expression. Then, the process proceeds to S202.

In S204, the model updating unit 308 of the health condition judgment model updating device 300 judges whether or not the prediction accuracy exceeds the judgment reference value. That is, the model updating unit 308 judges whether or not the accuracy of the reconstructed model exceeds the accuracy of the model before reconstruction. When the judgment result is "Yes", that is, when the accuracy of the reconstructed model exceeds the accuracy of the model before reconstruction, the process proceeds to S206. When the judgment result is "No", that is, when the accuracy of the reconstructed model does not exceed the accuracy of the model before reconstruction, the process proceeds to S208.

In S206, the model updating unit 308 of the health condition judgment model updating device 300 updates the model by using the learned model that was obtained in S202 as a new prediction model. Then, the model updating process is terminated.

In S208, the model updating unit 308 of the health condition judgment model updating device 300 learns by using the changed parameter and by changing the learned data. That is, in the same manner as the above (M2) method, the model is reconstructed by preparing data that is different from the data that was used for learning in the past. In addition, the model updating unit 308 may learn by using data that has been accumulated after the time point at which the model updating unit 308 learned last time. Then, the process proceeds to S210.

In S210, the model updating unit 308 of the health condition judgment model updating device 300 judges whether or not the prediction accuracy exceeds the judgment reference value. That is, the model updating unit 308 judges whether or not the accuracy of the reconstructed model exceeds the accuracy of the model before reconstruction. When the judgment result is "Yes", that is, when the accuracy of the reconstructed model exceeds the accuracy of the model before reconstruction, the process proceeds to S206. When the judgment result is "No", that is, when the accuracy of the reconstructed model does not exceed the accuracy of the model before reconstruction, the process proceeds to S212.

In S212, the model updating unit 308 of the health condition judgment model updating device 300 judges whether or not all the parameters that define the model have been changed. When the judgment result is "Yes", that is, when all the parameters that define the model have already been changed, the process proceeds to S214. When the judgment result is "No", that is, when not all the parameters that define the model have been changed, the process returns to S202, and a parameter that is different from the previous one is changed.

In S214, the model updating unit 308 of the health condition judgment model updating device 300 compares accuracies (accuracy rates) for models with each other and adopts as the model the one that has the highest accuracy. Then, the process proceeds to S206. The models that are compared with each other in this step may be models that were obtained in step S208 or may be models that were obtained in step S202 and step S208.

Figure 12:
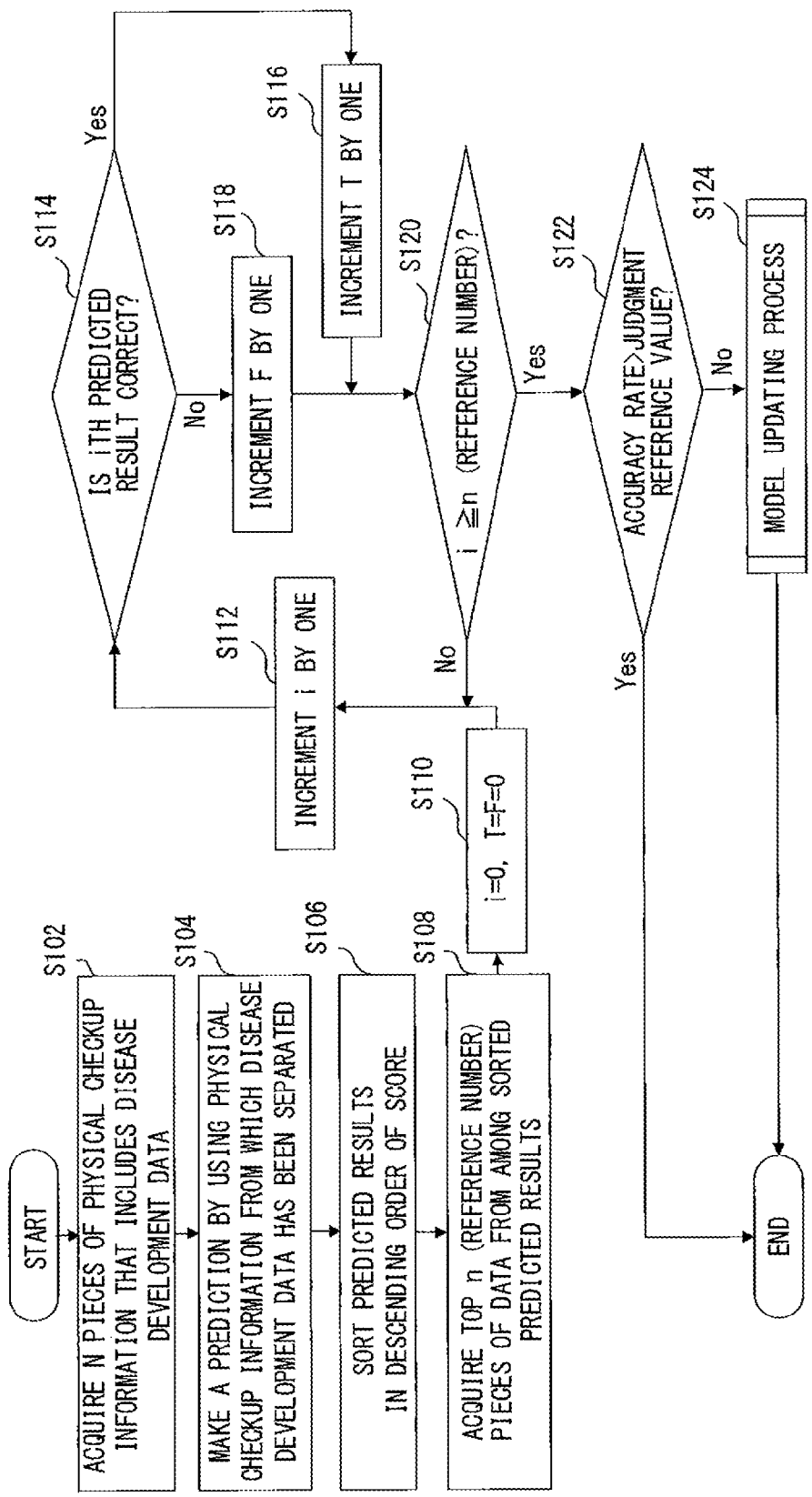
FIG. 12 is a flowchart illustrating an example of a model updating judgment process flow in the health condition judgment model updating method.

When the model updating process is terminated, the process returns to FIG. 12.

When the model updating unit 308 of the health condition judgment model updating device 300 terminates the process in S124 in FIG. 12, the process is terminated.

As described, the accuracy rate for the entirety of the population is not calculated. The accuracy (accuracy rate) is calculated according to a specified number of pieces of data that are a portion of the data of the population, and it is judged whether or not to update the model according to the calculated accuracy (accuracy rate). By adopting such a method or by using a device that adopts such a method, it is possible to maintain the accuracy of predictions that are made by using the health condition judgment model. Here, pieces of data that are a portion of the data of the population may be a top group of the pieces of data when the predicted results for the entirety of the population are ranked according to score.

In general, from among the predicted results for the entirety of the population, only some (for example, the top 100 people for whom disease development likelihoods are extremely high) are meaningful in reality. There are cases in which even though the accuracy rate for certain pieces of data that are meaningful in reality is low, the accuracy rate for the entirety of the population looks high depending on the accuracy rate for the rest of the pieces of data of the entirety of the population, and vice versa. However, in the above method, it is possible to avoid missing the timing at which the model is to be updated or to avoid updating the model even though it is not necessary to do so due to making a judgment on model update necessity according to the accuracy rate for the entirety of the population. In addition, in the above method, it is possible to decide on the model update timing so as to maintain the accuracy rate for some meaningful prediction targets in the population.

In the above, it is assumed that some of the pieces of data of the population that are used for accuracy (accuracy rate) calculation are the top N (N is an arbitrary integer) pieces of data in descending order of score. However, it may also be assumed that pieces of data that have a score that is greater than or equal to S (S is a specified value of score) are used.

<Comparative Example>

A comparative example will be described with reference to FIGS. 14 and 15.

In the comparative example, accuracy (accuracy rate) is predicted by using all the pieces of data of the population, and it is judged whether or not to update the model.

Figure 14:
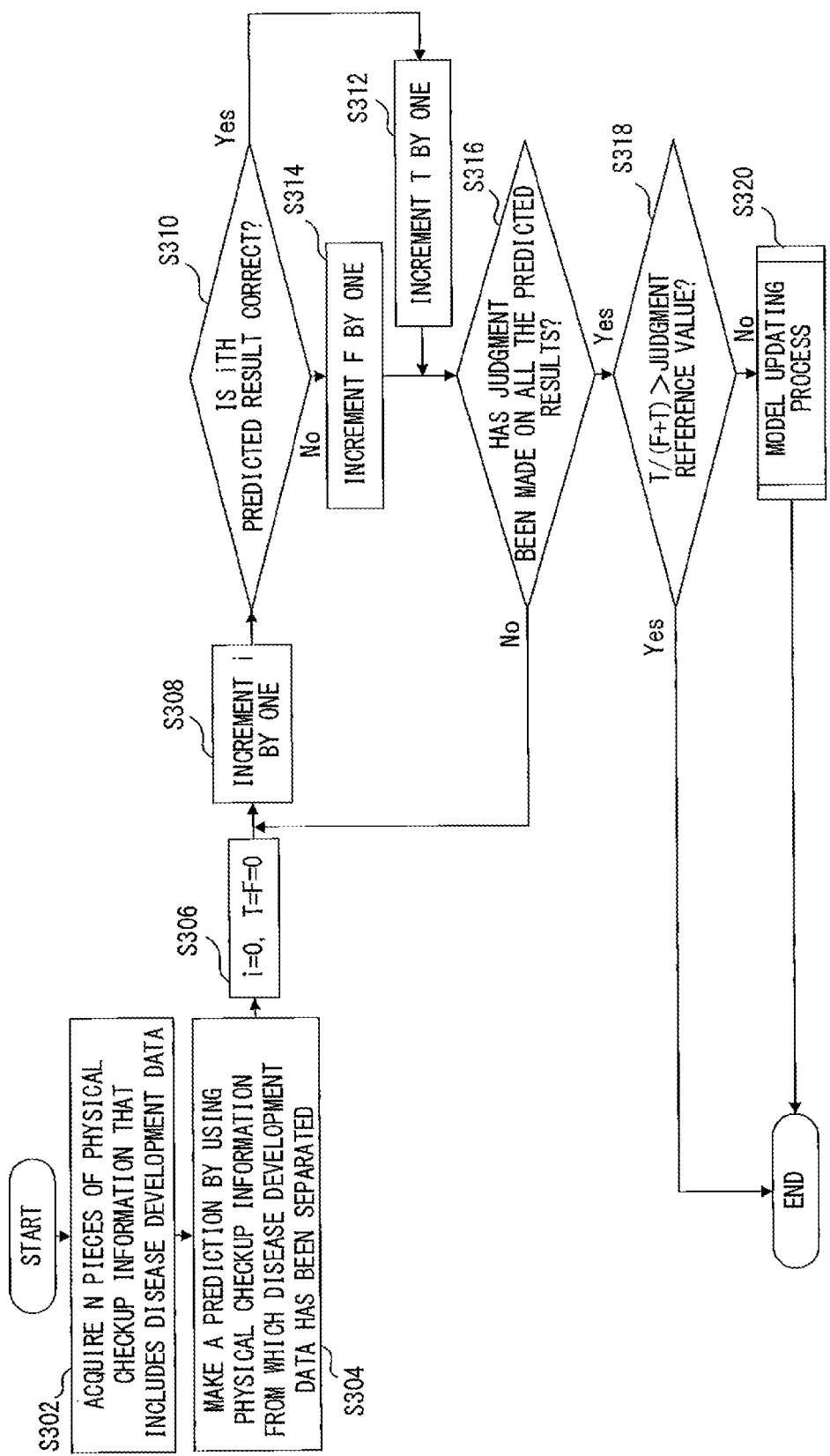
FIG. 14 is a flowchart illustrating a comparative example of the model updating judgment process flow in the health condition judgment model updating device.

FIG. 14 is a flowchart illustrating the comparative example of the model update judging process flow.

The flowchart illustrated in FIG. 14 is obtained by deleting the processes in steps S106 to S108 from the flowchart illustrated in FIG. 12 and using not the reference number of pieces of data but all the pieces of data of the entirety of the population in order to calculate the accuracy rate.

The health condition judgment model updating device that performs the process in FIG. 14 is hereinafter referred to as a health condition judgment model updating device 600.

When the process is started, first, in S302, the health condition judgment model updating device 600 acquires N pieces of physical checkup information that include disease development data. This process corresponds to S102 in FIG. 12. Then, the process proceeds to S304.

In S304, the health condition judgment model updating device 600 makes a prediction by using physical checkup information from which disease development data has been separated. This process corresponds to S104 in FIG. 12. Then, the process proceeds to S306.

In S306, the health condition judgment model updating device 600 resets dummy variables i, T, and F so that i=1, and T=F=0. This process corresponds to S110 in FIG. 12. Here, dummy variables i, T, and F are integers. Dummy variable i is used for specifying one of the predicted results. Dummy variable T is used for indicating the number of predicted results that have turned out to be correct. Dummy variable F is used for indicating the number of predicted results that have turned out to be wrong. Then, the process proceeds to S308.

In S308, the health condition judgment model updating device 600 increments the value of dummy variable i by one. Then, the process proceeds to S310.

In S310, the health condition judgment model updating device 600 judges whether or not the i-th predicted result is correct. When the judgment result is "Yes", that is, when the i-th predicted result is correct, the process proceeds to S312. When the judgment result is "No", that is, when the i-th predicted result is wrong, the process proceeds to S314.

In S312, the health condition judgment model updating device 600 increments the value of dummy variable T by one. Then, the process proceeds to S316.

In S314, the health condition judgment model updating device 600 increments the value of dummy variable F by one. Then, the process proceeds to S316.

In S316, the health condition judgment model updating device 600 judges whether or not judgments have been made on all the pieces of data of the predicted results. When the judgment result is "Yes", that is, when judgments have been made on all the pieces of data of the predicted results, the process proceeds to S318. When the judgment result is "No", that is, when judgments have not been made on all the pieces of data of the predicted results, the process returns to S310.

In addition, the health condition judgment model updating device 600 may calculate the accuracy rate $T/n(=T/(T+F))$ after the result has been judged to be "Yes", that is, after judgments have been made on all the pieces of data of the predicted results.

In S318, the health condition judgment model updating device 600 judges whether or not the accuracy rate $T/n(=T/(T+F))$ is greater than the judgment reference value. When the judgment result is "Yes", that is, when the accuracy rate T/n is greater than the judgment reference value, the process is terminated. When the judgment result is "No", that is, when the accuracy rate T/n is not greater than the judgment reference value, the process proceeds to S320.

In S310, the health condition judgment model updating device 600 performs a model updating process. Since the process in this step is the same as or similar to that illustrated in FIG. 13, the description thereof will be omitted.

When the process in S310 has been terminated, the health condition judgment model updating device 600 terminates the process.

FIG. 15 illustrates the result that is obtained by applying the above process that is performed by the health condition judgment model updating device 600 to the examples of the judgment results of the predicted results that are illustrated in FIG. 7. FIG. 15 is a diagram illustrating the accuracy rate for the predicted results in the comparative example.

The accuracy rate for the predicted results on the subjects with IDs 0001 to 0010 is 80%. Here, in the example illustrated in FIG. 15, the model is not updated in the case in which the judgment reference value is 80%.

The result illustrated in FIG. 9 is obtained by using pieces of data of people who have extremely high disease development likelihoods according to the predicted result. That is, the result illustrated in FIG. 9 is obtained by using pieces of data of people for whom it is actually possible to provide guidance on physical checkup results. Therefore, it is possible to decide on the model update timing so that the accuracy rate may be maintained for some meaningful prediction targets in the population by judging the necessity of a model update by using the result illustrated in FIG. 9.

<Modification>

A health condition judgment model updating device 300' and a health condition judgment model updating method will be described with reference to FIG. 4 and FIGS. 16-19.

In this example, pieces of data that are obtained after some measures have been taken for the data, for example, pieces of data of subjects for whom health guidance has been provided, are excluded from accuracy rate calculation targets.

It is considered the future condition that is indicated by data of a subject for whom measures have been taken, for example, for whom health guidance has been provided, is artificially changed from the future condition that the original data of the subject indicated. That is, the data is considered to be changed so that it is less likely to develop a disease. It is highly likely that such data will not fall under a "disease development" condition in the future even though the current score is disadvantageous. Therefore, such data is excluded as "exceptional data" from data for accuracy rate calculation. That is, "exceptional data" may be data of a subject for whom health guidance has been performed.

In FIG. 4, the health condition judgment model updating device 300' of this example includes the predicting unit 302, the predicted result judging unit 304', the model update judging unit 306, and the model updating unit 308.

The predicted result judging unit 304' uses data that is obtained by excluding exceptional data when the accuracy rate is calculated. The predicted result judging unit 304' calculates the accuracy rate by excluding, from a plurality of pieces of data that relate to a plurality of subjects, pieces of data that correspond to subjects for whom guidance has already been provided from among the plurality of subjects.

The health condition judgment model updating device 300' may be realized as the general-purpose computer 500.

Figure 16:
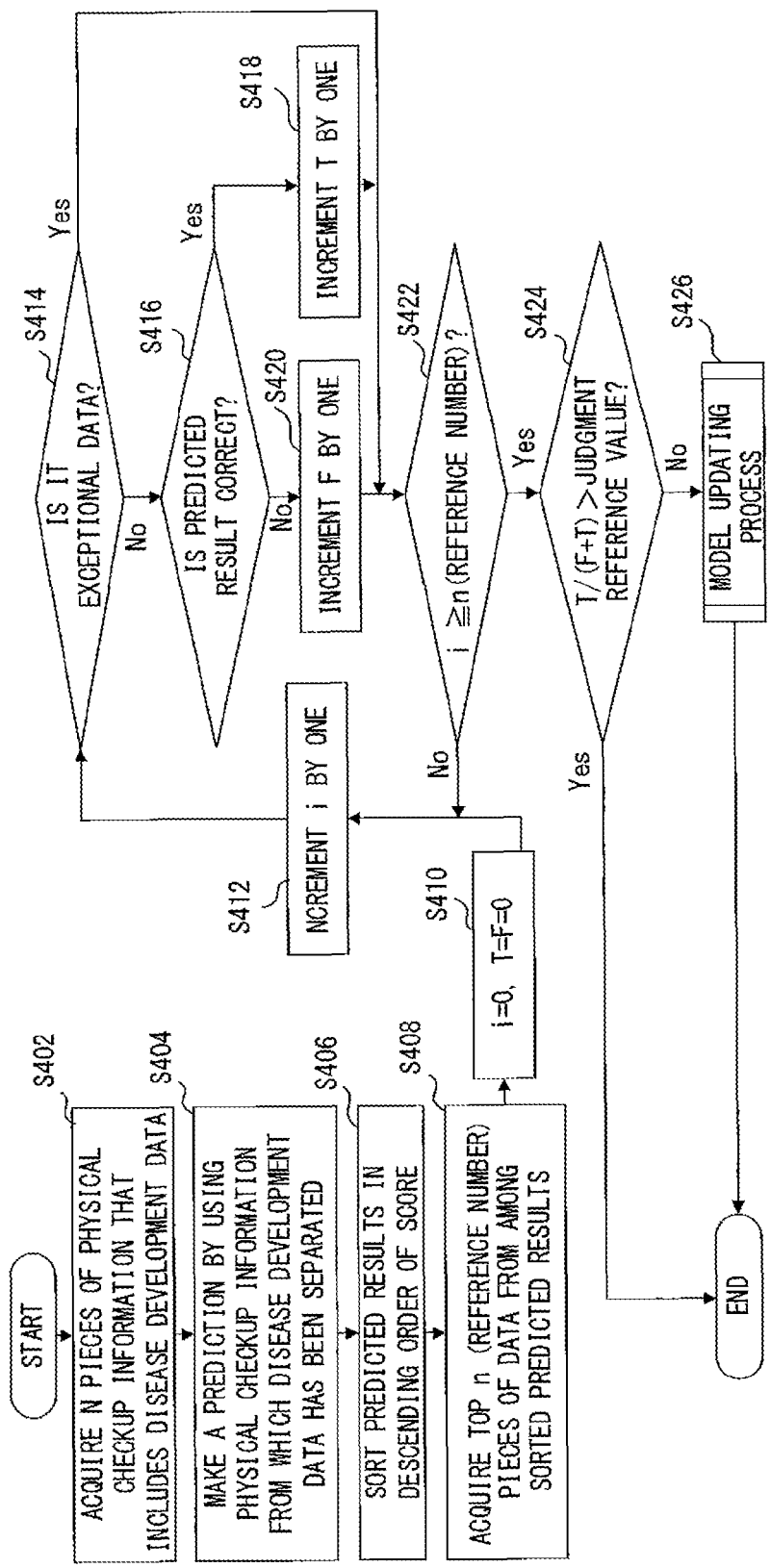
FIG. 16 is a flowchart illustrating an example of a model updating judgment process flow in a health condition judgment model updating method of a modification.

FIG. 16 is a flowchart illustrating an example of a model update judging process flow in the health condition judgment model updating method of a modification.

When the process is started, first, in S402, the predicting unit 302 of the health condition judgment model updating device 300' acquires N pieces of physical checkup information that includes disease development data. This process corresponds to S102 in FIG. 12. Then, the process proceeds to S404.

In S104, the predicting unit 302 of the health condition judgment model updating device 300' makes a prediction according to physical checkup information from which disease development data has been separated. This process corresponds to S104 in FIG. 12. Then, the process proceeds to S406.

In S406, the predicting unit 302 of the health condition judgment model updating device 300' sorts predicted results in descending order of score. Examples of the predicted results that are sorted in descending order of score are illustrated in FIG. 8. This process corresponds to S106 in FIG. 12. Then, the process proceeds to S408.

In S408, the predicting unit 302 of the health condition judgment model updating device 300' acquires the top n (reference number) predicted results from among the sorted predicted results. FIG. 8 illustrates the example of acquiring the top five predicted results. This process corresponds to S108 in FIG. 12. Then, the process proceeds to S410.

In S410, the predicted result judging unit 304' of the health condition judgment model updating device 300' resets dummy variables i, T, and F so that i=1, and T=F=0. This process corresponds to S110 in FIG. 12. Dummy variables i, T, and F are integers. Dummy variable i is used for specifying one of the predicted results. Dummy variable T is used for indicating the number of predicted results that have turned out to be correct. Dummy variable F is used for indicating the number of predicted results that have turned out to be wrong. Then, the process proceeds to S412.

In S412, the predicted result judging unit 304' of the health condition judgment model updating device 300' increments the value of dummy variable i by one. This process corresponds to S112 in FIG. 12. Then, the process proceeds to S414.

In S414, the predicted result judging unit 304' of the health condition judgment model updating device 300' judges whether or not the i-th predicted result is exceptional data. When the judgment result is "Yes", that is, when the i-th predicted result is exceptional data, the process proceeds to S422. When the judgment result is "No", that is, when the i-th predicted result is not exceptional data, the process proceeds to S416.

In S416, the predicted result judging unit 304' of the health condition judgment model updating device 300' judges whether or not the i-th predicted result is correct. This process corresponds to S114 in FIG. 12. When the judgment result is "Yes", that is, when the i-th predicted result is correct, the process proceeds to S418. When the judgment result is "No", that is, when the i-th predicted result is wrong, the process proceeds to S420.

In S418, the predicted result judging unit 304' of the health condition judgment model updating device 300' increments the value of dummy variable T by one. This process corresponds to S116 in FIG. 12. Then, the process proceeds to S422.

In S410, the predicted result judging unit 304' of the health condition judgment model updating device 300' increments the value of dummy variable F by one. This process corresponds to S118 in FIG. 12. Then, the process proceeds to S422.

In S422, the predicted result judging unit 304' of the health condition judgment model updating device 300' judges whether or not dummy variable i is greater than or equal to reference number n. This process corresponds to S120 in FIG. 12. When the judgment result is "Yes", that is, when dummy variable i is greater than or equal to reference number n, the process proceeds to S424. When the judgment result is "No", that is, when dummy variable i is not greater than or equal to reference number n, the process returns to S412.

In addition, in S422, the predicted result judging unit 304' of the health condition judgment model updating device 300' may calculate the accuracy rate $T/n(=T/(T+F))$ after the result has been judged to be "Yes", that is, after dummy variable i has been judged to be greater than or equal to reference number n.

In S424, the model update judging unit 306 of the health condition judgment model updating device 300' judges whether or not the accuracy rate $T/n(=T/(T+F))$ is greater than the judgment reference value. This process corresponds to S122 in FIG. 12. When the judgment result is "Yes", that is, when the accuracy rate $T/n$ is greater than the judgment reference number, the process is terminated. When the judgment result is "No", that is, when the accuracy rate $T/n$ is not greater than the judgment reference value, the process proceeds to S426.

In S426, the model updating unit 308 of the health condition judgment model updating device 300' performs a model updating process. Since the process in this step is the same as or similar to that illustrated in FIG. 13, the description thereof will be omitted.

When the process in S426 is terminated, the health condition judgment model updating device 300' terminates the process.

Figure 17:
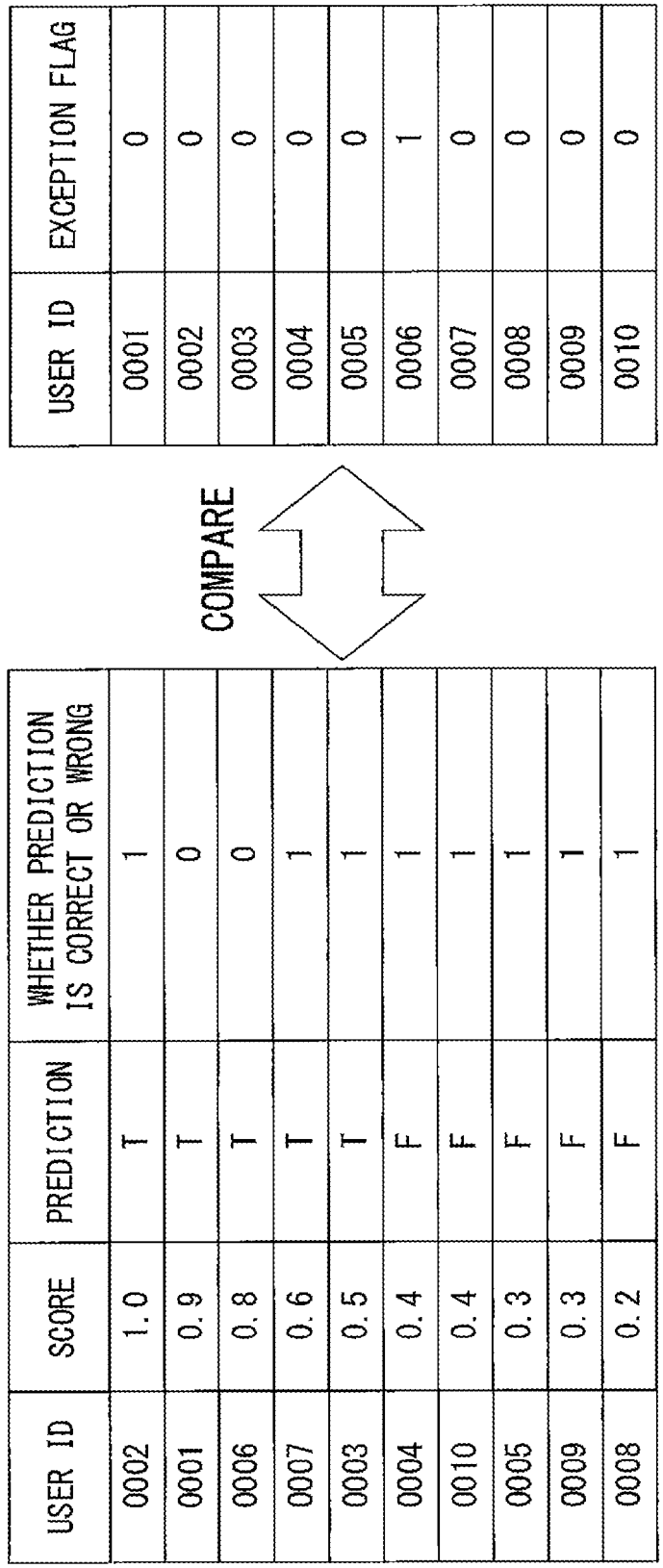
FIG. 17 is a diagram illustrating a state in which predicted results are compared with actual diagnoses in the health condition judgment model updating device of the modification.

FIG. 17 is a diagram illustrating a state in which predicted results are compared with actual diagnoses in the health condition judgment model updating device of the modification. In FIG. 17, the results illustrated in FIG. 7 are compared with a table that indicates whether or not apiece of data that corresponds to a subject with a user ID is exceptional data. Whether or not a piece of data of a subject with a user ID is exceptional data may be judged according to whether an exception flag is "1" or "0". An exception flag of "1" means that the piece of data in question is the data of a subject for whom health guidance has been performed.

Figure 18:
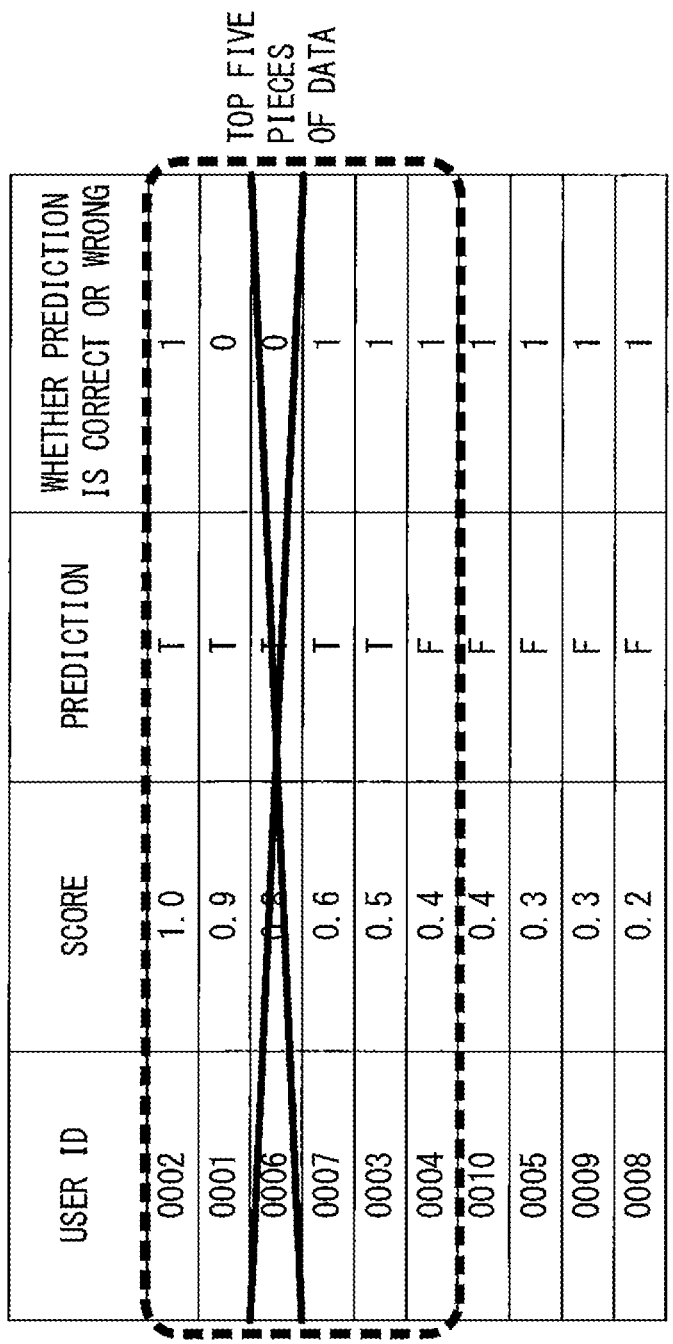
FIG. 18 is a diagram illustrating examples of judgment results on predicted results in the health condition judgment model updating device of the modification.

FIG. 19 is a diagram illustrating the accuracy rate for the top five pieces of data in the health condition judgment model updating device of the modification. When pieces of data are arranged in descending order of score, since the piece of data of user ID 0006 is exceptional data, the piece of data is not used for accuracy rate calculation as depicted in FIG. 18. Then, the top five pieces of data in descending order of score are five pieces of data that correspond to user IDs "0002", "0001", "0007", "0003", and "0004", respectively. The accuracy rate that is calculated from the pieces of data is 80%, as illustrated in FIG. 19.

In the above example, the results illustrated in FIG. 15 and the result illustrated in FIG. 19 coincide with each other by chance. The result illustrated in FIG. 19 is obtained by using pieces of data of people who have extremely high disease development likelihoods according to predicted results and for whom health guidance has not performed. That is, the result illustrated in FIG. 19 is obtained by using pieces of data of people for whom it is actually possible to provide guidance on physical checkup results. Therefore, it is possible to decide on the model update timing so that the accuracy rate may be maintained for some meaningful prediction targets in the population by judging the need for a model update by using the result illustrated in FIG. 19.

According to the embodiments, it is possible to judge whether or not it is necessary to update (recreate) the model that has been established.

Note that the present invention is not limited to the embodiments described above and various configurations and embodiments can be made without departing from the spirit and scope of the invention.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A model updating method that is executed by a computer, the model updating method comprising:
    by using the computer, calculating a score that indicates a degree of normality or abnormality of each of a plurality of pieces of data by using each of the plurality of pieces of data as a judgment model;
    by using the computer, predicting as a predicted condition whether each of the plurality of pieces of data is normal or abnormal according to the score;
    by using the computer, first judging whether or not the predicted condition is correct for each of the plurality of pieces of data;
    by using the computer, calculating an accuracy rate for the predicted conditions of a top specified number of pieces of the data in order of decreasing abnormality as indicated by the score when the plurality of pieces of data are arranged in a specified order of score, the accuracy rate being calculated by excluding from the plurality of pieces of data pieces of data that are obtained after measures have already been taken for the plurality of pieces of data; and
    by using the computer, second judging whether or not it is necessary to update the judgment model according to the accuracy rate.

2. The model updating method according to claim 1, wherein
    the judgment model includes a parameter and the parameter is calculated by using learned data, and
    the model updating method further comprising:
    updating the judgment model so that the accuracy rate is improved by changing at least one of the parameter and the learned data when it has been judged that it is necessary to update the judgment model.

3. The model updating method according to claim 1, wherein
    the plurality of pieces of data include physical checkup results of a plurality of subjects and the predicted condition relates to a presence or absence of development of a disease of each of the plurality of subjects.

4. A model updating device comprising:
    a processor that executes a process including:
        calculating a score that indicates a degree of normality or abnormality of each of a plurality of pieces of data by using each of the plurality of pieces of data as a judgment model;
        predicting as a predicted condition whether each of the plurality of pieces of data is normal or abnormal according to the score;
        first judging whether or not the predicted condition is correct for each of the plurality of pieces of data;
        calculating an accuracy rate for the predicted conditions of a top specified number of pieces of the data in order of decreasing abnormality as indicated by the score when the plurality of pieces of data are arranged in a specified order of score, the accuracy rate being calculated by excluding from the plurality of pieces of data pieces of data that are obtained after measures have already been taken for the plurality of pieces of data; and
        second judging whether or not it is necessary to update the judgment model according to the accuracy rate.

5. The model updating device according to claim 4, wherein
    the judgment model includes a parameter and the parameter is calculated by using learned data, and
    the process further including:
    updating the judgment model so that the accuracy rate is improved by changing at least one of the parameter and the learned data when it has been judged that it is necessary to update the judgment model.

6. The model updating device according to claim 4, wherein
    the plurality of pieces data include physical checkup results of a plurality of subjects and the predicted condition relates to a presence or absence of development of a disease of each of the plurality of subjects.

7. A non-transitory computer-readable recording medium having stored therein a control program for causing a computer to execute a process, the process comprising:
- calculating a score that indicates a degree of normality or abnormality of each of a plurality of pieces of data by using each of the plurality of pieces of data as a judgment model;
- predicting as a predicted condition whether each of the plurality of pieces of data is normal or abnormal according to the score;
- first judging whether or not the predicted condition is correct for each of the plurality of pieces of data;
- calculating an accuracy rate for the predicted conditions of a top specified number of pieces of the data in order of decreasing abnormality as indicated by the score when the plurality of pieces of data are arranged in a specified order of score, the accuracy rate being calculated by excluding from the plurality of pieces of data pieces of data that are obtained after measures have already been taken for the plurality of pieces of data; and
- second judging whether or not it is necessary to update the judgment model according to the accuracy rate.

8. The non-transitory computer-readable recording medium according to claim 7, wherein the judgment model includes a parameter and the parameter is calculated by using learned data, and the process further includes:

updating the judgment model so that the accuracy rate is improved by changing at least one of the parameter and the learned data when it has been judged that it is necessary to update the judgment model.

9. The non-transitory computer-readable recording medium according to claim 7, wherein the plurality of pieces of data include physical checkup results of a plurality of subjects and the predicted condition relates to a presence or absence of development of a disease of each of the plurality of subjects.

* * * * *